(12) United States Patent
Bolle et al.

(10) Patent No.: US 10,988,758 B2
(45) Date of Patent: Apr. 27, 2021

(54) MAGNETIC NANOPARTICLES FOR NUCLEIC ACID PURIFICATION

(71) Applicant: Roche Molecular Systems, Inc., Pleasanton, CA (US)

(72) Inventors: Jens Christian Bolle, Penzberg (DE); Thomas Walter, Penzberg (DE); Peter Wenzig, Munich (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 169 days.

(21) Appl. No.: 16/106,451

(22) Filed: Aug. 21, 2018

(65) Prior Publication Data
US 2019/0002871 A1   Jan. 3, 2019

Related U.S. Application Data

(62) Division of application No. 14/637,014, filed on Mar. 3, 2015, now Pat. No. 10,100,301.

(30) Foreign Application Priority Data

Mar. 4, 2014   (EP) .................................... 14157699

(51) Int. Cl.
| | |
|---|---|
| *B01J 20/06* | (2006.01) |
| *C12N 15/10* | (2006.01) |
| *B01J 20/28* | (2006.01) |
| *B01J 20/32* | (2006.01) |
| *B01J 20/10* | (2006.01) |
| *C12Q 1/6806* | (2018.01) |
| *H01F 1/00* | (2006.01) |

(52) U.S. Cl.
CPC .......... *C12N 15/1013* (2013.01); *B01J 20/06* (2013.01); *B01J 20/103* (2013.01); *B01J 20/28009* (2013.01); *B01J 20/28016* (2013.01); *B01J 20/3293* (2013.01); *C12Q 1/6806* (2013.01); *H01F 1/0054* (2013.01)

(58) Field of Classification Search
CPC ..... C12N 15/1013; B01J 20/06; B01J 20/103; B01J 20/28009; B01J 20/28016; B01J 20/3293; C12Q 1/6806; H01F 1/0054
See application file for complete search history.

(56) References Cited

U.S. PATENT DOCUMENTS

| 5,698,271 A | 12/1997 | Liberti et al. |
| 2011/0206619 A1 | 8/2011 | Mahmoudi et al. |
| 2011/0207869 A1* | 8/2011 | Katusic .................. C01G 49/00 524/442 |

FOREIGN PATENT DOCUMENTS

| WO | 1998051435 A1 | 11/1998 |
| WO | 2013123525 A1 | 8/2013 |

OTHER PUBLICATIONS

Gupta, et al., "Synthesis and surface engineering of iron oxide nanoparticles for biomedical applications," Biomaterials 26(18):3995-4021 (2005).
Kempe, et al., "The use of magnetite nanoparticles for implant-assisted magnetic drug targeting in thrombolytic therapy," Biomaterials 31(36):9499-9510 (2010).
Kim, et al., "Multifunctional uniform nanoparticles composed of a magnetite nanocrystal core and a mesoporous silica shell for magnetic resonance and fluorescence imaging and for drug delivery," Angew. Chem. Int. Ed. Engl. 47(44):8438-8441 (2008).
Liu, et al., "Shape Evolution and Tunable Properties of Monodisperse Magnetite Crystals Synthesized by a Facile Surfactant-Free Hydrothermal Method," Eur. J. Inorg. Chem. 2010:4499-4505 (2010).
Narayanan, et al., "Enhanced bio-compatability of ferrofluids of self-assembled superparamagnetic iron oxide-silica core-shell nanoparticles," J. Nanosci. Nanotechnol. 11(3):1958-1967 (2011).

* cited by examiner

*Primary Examiner* — Jezia Riley
(74) *Attorney, Agent, or Firm* — Eric Grant Lee (57) ABSTRACT

The present invention relates to monodisperse silanized ferrimagnetic iron oxide particles, a method for producing the same and a method for independent generic binding of nucleic acid molecules to the particles.

4 Claims, 5 Drawing Sheets

MAGNETIC NANOPARTICLES FOR NUCLEIC ACID PURIFICATION

CROSS REFERENCE TO RELATED APPLICATIONS

This application is a divisional patent application of U.S. patent application Ser. No. 14/637,014, filed Mar. 3, 2015, which claims the benefit of priority under 35 U.S.C. § 119 of EP 14157699.1, filed Mar. 4, 2014, both of which are incorporated herein by reference in their entireties.

FIELD OF THE INVENTION

The present invention relates to monodisperse silanized ferrimagnetic iron oxide particles, a method for producing the same and their use for independent generic binding nucleic acid molecules.

BACKGROUND OF THE INVENTION

Magnetic nanoparticles are widely used in the field of nucleic acid purification. All commercially available large scale magnetic nanoparticles have superparamagnetic properties. In contrast, ferrimagnetic nanoparticles are not commercially available and only known from academic publications. Such publications include nanoparticles with silica coatings (Chen et al; J. of alloys and compounds 497 (2010) 221-227; Wang et al; Bioresource Technology 101 (2010) 8931-8935; Reza et al; Cent. Eu. J. Chem 5 (2010) 1041-1048). One of the major drawbacks of the majority of preparations of ferrimagnetic nanoparticles known in the art where low pressure reactors at <100° C. are used is that the synthesis is difficult to upscale and automate (Wang et al; Bioresource Technology 101 (2010) 8931-8935; Reza et al; Cent. Eu. J. Chem 5 (2010) 1041-1048).

The use of glycols as solvent and reducing agent for the synthesis of ferrimagnetic nanoparticles has been shown (Wiley et al; Nano Lett. 4 (2004) 1733-1739; D. Larcher, R. J. Partrice; J. Solid State Chem. 154 (2000) 405-411; Gai et al; J. Phys. D: Appl. Phys. 43 (2010) 445-553)—also in combination with the surfactant-free synthesis route ("Green synthesis route") (Liu et al; Eur. J. Inorg. Chem. 2 (2010) 4499-4505). These preparations are focused on the use of iron(III) salts which result in poor size distribution and yield when upscaled to more than 100 mL scale.

Silanization of ferrimagnetic nanoparticles is only known in the art according to the Stöber method which relies on harmful alkoxy silanes. Using harmless $SiO_2$ solution in purely aqueous conditions have only been shown in the context of superparamagnetic particles (Philipse et al; Langmuir 10 (1994) 92-99).

Extraction of nucleic acids by means of hydrothermally prepared ferrimagnetic particle structures are described (Gai et al; J. Phys. D: Appl. Phys. 43 (2010) 445-553). These publications used ferrimagnetic particles which were produced by silane chemistry or without silicone containing coating, wherein the production was complex or resulted in a poor eluation.

The object of the present invention is the provision of monodisperse silanized ferrimagnetic iron oxide particles for nucleic acid binding which do not show the above mentioned drawbacks and a method for producing the same.

SUMMARY OF THE INVENTION

It was found that silanized ferrimagnetic iron oxide particles for independent generic nucleic acid binding can be produced with a high degree of uniformity (very defined reproducible diameters of the particles), a high yield and homogeniously high magnetization saturations. Furthermore it was found that silanizing can be performed resulting in a very dense layer of silicate around the magnetite core of the particles, such that the quality of silanization is comparable to the quality reached by known processes, however, with less harmful chemicals and more cost effective educts as compared to the known processes.

The present invention thus relates to a method for producing a plurality of silanized ferrimagnetic iron oxide particles for independent generic nucleic acid binding, wherein the method comprises the steps of a) adding an iron(II) salt to a liquid glycol to obtain a solution, b) raising the pH of the solution to a value of at least 9 such that a precipitate is obtained, wherein during steps a) and b) a first temperature is applied to the solution and wherein during steps a) and b) the solution is gassed with nitrogen, c) mixing the solution comprising the precipitate at a second temperature such that ferrimagnetic iron oxide particles are obtained, and d) contacting the ferrimagnetic iron oxide particles with a silicate solution such that silanized ferrimagnetic iron oxide particles are obtained. In one embodiment the step of contacting the ferrimagnetic iron oxide particles with a silicate solution comprises the steps of d1) sonificating the silicate solution comprising the ferrimagnetic iron oxide particles, d2) lowering the pH of the silicate solution to a value of 6 or below such that silanized ferrimagnetic iron oxide particles are obtained, d3) washing of the silanized ferrimagnetic particles with water, and d4) washing of the silanized ferrimagnetic particles with isopropanol such that crosslinking occurs within the silicate layer.

The present invention further relates to monodisperse silanized ferrimagnetic iron oxide particles for independent generic nucleic acid binding comprising a core, wherein the core comprises an inner layer comprising $Fe_3O_4$ and an outer layer comprising $Fe_2O_3$, a coating, wherein the coating comprises silica and silicates from sodium silicate precipitation, wherein the particles display a sedimentation speed in pure water of less than 60 µm/s, and no significant iron bleeding particles in 1M HCl for at least 60 min.

The present invention further relates to a method for independent generic binding of nucleic acid molecules to a composition comprising, contacting a sample containing nucleic acid molecule to the composition, wherein the composition comprises monidisperse silanized ferrimagnetic iron oxice particles, wherein said particles comprise a core, wherein the core comprises an inner layer comprising $Fe_3O_4$ and an outer layer comprising $Fe_2O_3$, a coating, wherein the coating comprises silica and silicates from sodium silicate precipitation, wherein the particles display a sedimentation speed in pure water of less than 60 µm/s, and no significant iron bleeding in 1M HCl for at least 60 minutes.

DETAILED DESCRIPTION OF THE INVENTION

The following definitions are set forth to illustrate and define the meaning and scope of various terms used to describe the invention herein.

The terms "a", "an" and "the" generally include plural referents, unless the context clearly indicates otherwise.

The term "acid" is used herein as known to the expert skilled in the art and refers to a substance capable of donating a proton in polar or non-polar solvents. The acid of choice for a particular reaction depends on the starting materials, the solvent and the temperature used for a specific reaction. Examples of acids include phosphoric acid, sulphuric acid and hydrochloric acid.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

In the context of the pH the below terms are defined as follows:
"At least": A "pH of at least 7" refers to a pH value of 7 or higher, e.g. a pH value of 7, 8, 9, 10, 11, 12, 13 or 14.
"Raise": "Raising the pH" refers to changing the pH from a lower value to a higher value, e.g. changing the pH from 7 to 8.
"Or below": A "pH of 7 or below" refers to a pH value of 7 or lower, e.g. a pH value of 1, 2, 3, 4, 5, 6 or 7.
"Lower": "Lowering the pH" refers to changing the pH from a higher value to a lower value, e.g. changing the pH from 8 to 7.

The term "base" is used herein as known to the expert skilled in the art and refers to a substance capable of accepting a proton in polar or non-polar solvents. The base of choice for a particular reaction depends on the starting materials, the solvent and the temperature used for a specific reaction. Examples of bases include carbonate salts such as potassium carbonate, potassium bicarbonate, sodium carbonate, sodium bicarbonate, and cesium carbonate; halides such as cesium fluoride; phosphates such as potassium phosphate, potassium dihydrogen phosphate, and potassium hydrogen phosphate; hydroxides such as lithium hydroxide, sodium hydroxide, and potassium hydroxide; disilylamides such as lithium hexamethyldisilazide, potassium hexamethyldisilazide, and sodium hexamethyldisilazide; trialkylamines such as triethylamine, diisopropylamine, and diisopropylethylamine; heterocyclic amines such as imidazole, pyridine, pyridazine, pyrimidine, and pyrazine; bicyclic amines such as DBN and DBU; and hydrides such as lithium hydride, sodium hydride, and potassium hydride. Examples of bases include alkali metal hydroxides as defined herein; alkali metal hydrides such as lithium, sodium, or potassium hydride; and nitrogen-containing bases such as lithium diisopropyl amide (LDA), lithium bis(trimethylsilyl)amide, sodium bis(trimethylsilyl)amide, and potassium bis(trimethylsilyl)amide; and the like. It will be apparent to a skilled practioner that individual base and solvent combinations can be preferred for specific reaction conditions depending on such factors as the solubility of reagents, reactivity of reagents with Isomidazolam or the solvent, and preferred temperature ranges.

The term "crosslinking" as used herein refers to a chemical process, wherein two or more molecules interact to form n-mers, wherein n>1. Such interaction can be a covalent bond, hydrophilic or hydrophobic, ionic or electrostatic, interaction.

The term "ferrimagnetic" as used herein refers to a material consisting of populations of atoms with opposing but unequally distributed magnetic moments. Thus resulting in a magnetic saturation and remanence once an external magnetic field was applied.

The term "independent generic nucleic acid binding" as used herein refers to binding of single stranded and/or double stranded nucleic acid molecules such as DNA and/or RNA. Binding of such molecules occur independently of properties of the nucleic acid molecules, such sequence, presence or absence of modifications and concentration.

The term "iron bleeding" as used herein refers to the solvation of iron ions into the surrounding solvation medium. The term "significant iron bleeding" as used herein refers to a iron ion concentration in the surrounding solvent detectable by light spectroscopic methods (UV/Vis-Spectroscopy). Spectroscopy was performed from 200 nm to 800 nm in a quarz glas cuvette with 1 cm transmission distance in a total volume of 3 mL 5% w/w particle after adding 5M HCl solution and shaking for 10 seconds followed by magnetic separation of the beads by using a Neodymium-Iron-Borum magnet (1 cm×1 cm×1 cm). After the blanking with pure water no peak larger than the background noise should be seen or identified by the analysis software over the whole spectrum.

The term "monodisperse" as used herein refers to particles of essentially the same size. The size of the monodisperse silanized ferrimagnetic iron oxide particles of one certain batch is essentially the same for all particles within that batch. Essentially the same size of the particles has to be interpreted in the context of this description such that the difference in size, i.e. difference in diameter, of the particles is in average smaller than 5% (coefficient of variation).

The terms "nucleic acid", "nucleic acid molecule" or "polynucleotide" can be used interchangeably and refer to a polymer that can be corresponded to a ribose nucleic acid (RNA) or deoxyribose nucleic acid (DNA) polymer, or an analog thereof. This includes polymers of nucleotides such as RNA and DNA, as well as synthetic forms, modified (e.g., chemically or biochemically modified) forms thereof, and mixed polymers (e.g., including both RNA and DNA subunits). Exemplary modifications include methylation, substitution of one or more of the naturally occurring nucleotides with an analog, internucleotide modifications such as uncharged linkages (e.g., methyl phosphonates, phosphotriesters, phosphoamidates, carbamates, and the like), pendent moieties (e.g., polypeptides), intercalators (e.g., acridine, psoralen, and the like), chelators, alkylators, and modified linkages (e.g., alpha anomeric nucleic acids and the like). Also included are synthetic molecules that mimic polynucleotides in their ability to bind to a designated sequence via hydrogen bonding and other chemical interactions. Typically, the nucleotide monomers are linked via phosphodiester bonds, although synthetic forms of nucleic acids can comprise other linkages (e.g., peptide nucleic acids as described in Nielsen et al. (Science 254:1497-1500, 1991). A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, and a primer. A nucleic acid can be, e.g., single-stranded, double-stranded, or triple-stranded and is not limited to any particular length. Unless otherwise indicated, a particular nucleic acid sequence comprises or encodes complementary sequences, in addition to any sequence explicitly indicated.

The term "plurality" as used herein refers to two or more items or components. Accordingly, the term "plurality of particles" refers to two or more particles, such as silanized ferromagnetic iron oxide particles.

As used herein, the term "precipitate" refers to the formation of solid, such as a particle, in a solution during a chemical reaction.

The term "sedimentation speed" as used herein refers to the speed (length/time) with which a particle, such as a silanized ferromagnetic iron oxide particle, sediments at a defined gravitational force within a liquid, such as pure water. If no value for a defined gravitational force is given, the gravitational force to be assumed for the given reaction is gravitation of earth, i.e. 1.0 g.

The term "silanized" as used herein refers to the formation of a top layer containing silicone which is crosslinked by oxygen.

In one aspect, the description refers to a method for producing a plurality of silanized ferrimagnetic iron oxide particles for independent generic nucleic acid binding, wherein the method comprises the steps of a) adding an iron(II) salt to a liquid glycol to obtain a solution, b) raising the pH of the solution to a value of at least 9 such that a precipitate is obtained, wherein during steps a) and b) a first temperature is applied to the solution and wherein during steps a) and b) the solution is gassed with nitrogen, c) mixing the solution comprising the precipitate at a second temperature such that ferrimagnetic iron oxide particles are obtained, and d) contacting the ferrimagnetic iron oxide particles with a silicate solution such that silanized ferrimagnetic iron oxide particles are obtained.

The addition of the iron(II) salt to the liquid glycol to obtain a solution as performed in step a) above has the advantage over the methods known in the art that it results in a better size control. Furthermore, gassing the solution with nitrogen leads to a higher yield.

In one embodiment, the step of contacting the ferrimagnetic iron oxide particles with a silicate solution comprises the steps of d1) sonificating the silicate solution comprising the ferrimagnetic iron oxide particles, d2) lowering the pH of the silicate solution to a value of 6 or below such that silanized ferrimagnetic iron oxide particles are obtained, d3) washing of the silanized ferrimagnetic particles with water, and d4) washing of the silanized ferrimagnetic particles with isopropanol such that crosslinking occurs within the silicate layer.

The crosslinking performed in step d4) results in a very dense layer of silicate around the magnetite core and in a silanization comparable to the Stober method. However, the crosslinking according to the present description is performed with harmless chemicals and cost effective educts.

In one embodiment, the iron(II) salt is soluble in the liquid glycol. In a specific embodiment, the iron(II) salt soluble in the liquid glycol is selected from the group consisting of $FeCl_2$, $FeSO_4$, $FeAc_2$ and the hydrated forms thereof. The term hydrated forms as used herein has to be understood as a compound which is formed by the addition of water. Possible hydrated forms according to the present description are $FeCl_2 \cdot n\, H_2O$, $FeO_4 \cdot n\, H_2O$, $FeAc_2 \cdot n\, H_2O$, wherein $n \geq 1$. Specific hydrated forms according to the present description are $FeCl_2 \cdot 4\, H_2O$, $FeSO_4 \cdot 4\, H_2O$, $FeAc_2 \cdot 4\, H_2O$. In a specific embodiment, the iron(II) salt soluble in the liquid glycol is $FeCl_2$ and hydrated forms thereof.

In one embodiment, the concentration of $FeCl_2 \cdot 4\, H_2O$ in the liquid glycol is from 50 mmol to 70 mmol. In a specific embodiment, the concentration of $FeCl_2 \cdot 4\, H_2O$ in the liquid glycol is from 55 mmol to 65 mmol. In a more specific embodiment, the concentration of $FeCl_2 \cdot 4\, H_2O$ in the liquid glycol is from 58 mmol to 62 mmol. In a specific embodiment, the concentration of $FeCl_2 \cdot 4\, H_2O$ in the liquid glycol is 61.9 mmol.

In a specific embodiment, the liquid glycol is an alkyl glycol and polymerized forms thereof. In a specific embodiment, the alkyl glycol is selected from the group consisting of ethylene glycol, diethylene glycol, triethylene glycol, tetraethylene glycol, propylene glycol, dipropylene glycol, tripropylene glycol, tetraproylene glycol, butylene glycol, dibutylene glycol, tributylene glycol, tetrabutylene glycol. In a more specific embodiment, the alkyl glycol is triethylene glycol.

In one embodiment, the pH of the solution in step b) is raised to a value of at least 9. In a specific embodiment, the pH of the solution in step b) is raised to a value of at least 10. In a more specific embodiment, the pH of the solution in step b) is raised to a value of 10.5.

In one embodiment, the pH of the solution in step b) is raised using a base. In a specific embodiment, the pH of the solution in step b) is raised using an alkaline metal hydroxide. In a more specific embodiment, the pH of the solution in step b) is raised using an alkaline metal hydroxide selected from the group consisting of lithium hydroxide, sodium hydroxide and potassium hydroxide.

In one embodiment, the first temperature has a value from 20 to 120° C. In a specific embodiment, the first temperature has a value from 40 to 120° C., from 60 to 120° C., from 80 to 120° C., or from 90 to 110° C. In a more specific embodiment, the first temperature has a value from 95 to 105° C. In an even more specific embodiment, the first temperature has a value of 100° C. The application of the first temperature results in the evaporation of excess water from the reaction and thus in higher magnetization rates due to less uncontrolled further oxidation of the magnetite produced during the reaction.

In one embodiment, the first temperature is maintained for 5 to 60 min. In specific embodiment, the first temperature is maintained for 10 to 50 min. In a more specific embodiment, the first temperature is maintained for 20 to 50 min, for 30 to 50 min or for 35 to 45 min. In an even more specific embodiment, the first temperature is maintained for 40 min.

In one embodiment the gassing with nitrogen is performed at a pressure of between 0.1 and 1.0 bar at the outlet valve. In a specific embodiment, the gassing with nitrogen is performed at a pressure of between 0.2 and 0.8 bar at the outlet valve. In a more specific embodiment, the gassing with nitrogen is performed at a pressure of between 0.3 and 0.6 bar at the outlet valve. In an even more specific embodiment, the gassing with nitrogen is performed at a pressure of between 0.35 and 0.45 bar at the outlet valve. In a specific embodiment, the gassing with nitrogen is performed at a pressure of 0.4 bar at the outlet valve. Gassing with nitrogen at the above mentioned pressure values reduces the oxygen present in the solution and thus reduces undesirable oxidation during precipitation of the particles. Thus, higher yields and homogeniously high magnetization saturations are achieved.

In one embodiment, the second temperature has a value from 150 to 300° C. In a specific embodiment, the second temperature has a value from 200 to 300° C., from 210 to 290° C., from 220 to 280° C., from 230 to 270° C. or from 240 to 260° C. In a more specific embodiment, the second temperature has a value of 250° C. The second temperature results in particles with defined reproducible diameters even at scales larger than 500 mL.

In one embodiment, the second temperature is maintained for 20 min to 48 h. In a specific embodiment, the second temperature is maintained for 20 min to 40 h, for 20 min to 30 h, for 20 min to 20 h, for 20 min to 10 h, for 20 min to 5 h, for 20 min to 2 h, for 30 min to 90 min, for 40 min to 90 min, for 50 min to 90 min, for 60 min to 90 min or for 70 min to 90 min. In a more specific embodiment, the second temperature is maintained for 80 min.

Figure 1:
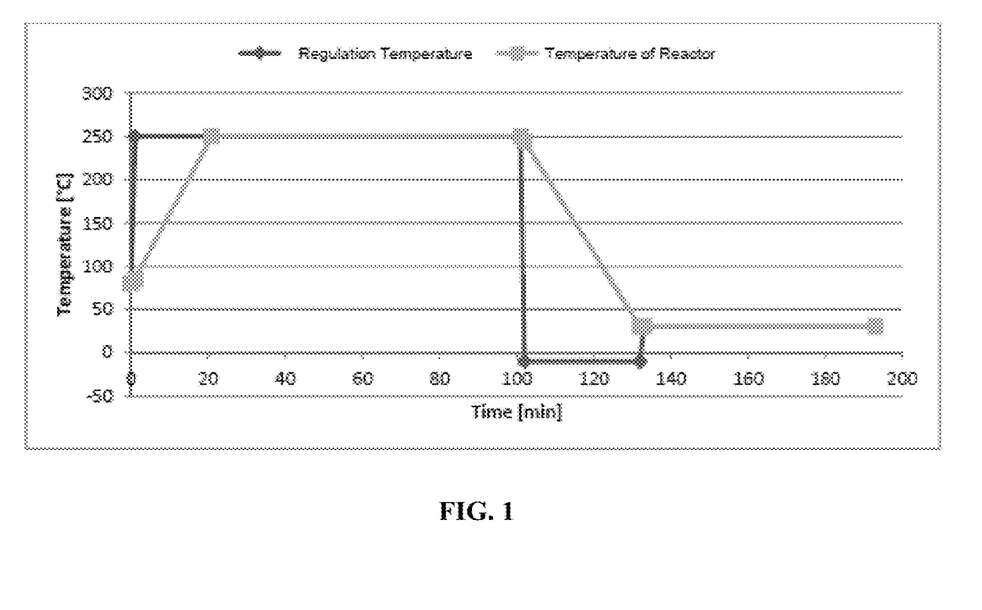
FIG. 1 Shows the regulation temperature and the resulting temperature of the reactor.

In a specific embodiment, the second temperature is regulated according to the following protocol. The second temperature starts at a value of 80° C. and is increased to a value of 250° C. within a time period of 20 min. The value of 250° C. is maintained for a time period of 80 min. Subsequently, the second temperature is decreased to a value of 30° C. within a time period of 35 min. The second temperature refers to the temperature within the reactor. The temperature gradient within the reactor and the actual regulation temperature is depicted in FIG. 1. The gradient as shown in the figure has to be accurately executes such that the controlled environment ensures the control of the reaction for forming particles with a homogeneous size distribution and high magnetization saturations.

In one embodiment, the silicate is selected from the group consisting of potassium silicate and sodium silicate. In a specific embodiment, the silicate is sodium silicate.

In one embodiment, the silicate is present in the solution in a concentration from 1 to 30% w/v. In a specific embodiment, the silicate is present in the solution in a concentration from 1 to 20% w/v, from 1 to 15% w/v, from 1 to 15% w/v, from 1 to 10% w/v, from 3 to 7% w/v or from 4 to 6% w/v. In a specific embodiment, the silicate is present in the solution in a concentration of 5.3% w/v.

In one embodiment, sonificating is performed with an amplitude of 60 to 100%. In a specific embodiment, sonificating is performed with an amplitude of 70 to 90%. In a more specific embodiment, sonificating is performed with an amplitude of 75 to 85%. In an even more specific embodiment, sonificating is performed with an amplitude of 80%. In one embodiment, sonificating is performed with a cycle of 10 to 30%. In a specific embodiment, sonificating is performed with a cycle of 15 to 25%. In a more specific embodiment, sonificating is performed with a cycle of 18 to 22%. In an even more specific embodiment, sonificating is performed with a cycle of 20%. In a specific embodiment, sonificating is performed with 80% of amplitude and 20% of cycle.

In one embodiment, sonificating is performed for a duration of 1 to 10 seconds. In a specific embodiment, sonificating is performed for a duration of 3 to 8 seconds. In a more specific embodiment, sonificating is performed for a duration of 4 to 6 seconds. In an even more specific embodiment, sonificating is performed for a duration of 5 seconds. In one embodiment, the sonificating pulses are interrupted by a pause of 30 to 70 seconds. In a specific embodiment, the sonificating pulses are interrupted by a pause of 40 to 60 seconds. In a more specific embodiment, the sonificating pulses are interrupted by a pause of 45 to 55 seconds. In an even more specific embodiment, the sonificating pulses are interrupted by a pause of 50 seconds. In a specific embodiment, sonificating is performed for a duration of 5 seconds followed by a pause of 50 seconds.

In one embodiment, the pH of the solution in step d2) is lowered to a value of 7 or below. In a specific embodiment, the pH of the solution in step d2) is lowered to a value of 6 or below. In a more specific embodiment, the pH of the solution in step d2) is lowered to a value of 5.

In one embodiment, the pH of the solution in step d2) is lowered using an acid selected from the group consisting of phosphoric acid, sulphuric acid and hydrochloric acid. In a specific embodiment, the pH of the solution in step d2) is lowered using any non-oxidizing and water-soluble acid. In a specific embodiment, the pH of the solution in step d2) is lowered using a non-oxidizing and water-soluble acid selected from the group consisting of hydrochloric acid, boric acid or prussic acid. In a specific embodiment, the pH of the solution in step d2) is lowered using hydrochloric acid. In another specific embodiment, the pH of the solution in step d2) is lowered using 1M hydrochloric acid.

In another embodiment, the method for producing a plurality of silanized ferrimagnetic iron oxide particles for independent generic nucleic acid binding comprises the steps of a) adding $FeCl_2$ or the hydrated forms thereof to triethylene glycol to obtain a solution, b) raising the pH of the solution to a value of 10.5 with sodium hydroxide such that a precipitate is obtained, wherein during steps a) and b) a first temperature is applied to the solution, wherein the first temperature has a value of 100° C. and is maintained for 40 min, and wherein during steps a) and b) the solution is gassed with nitrogen at a pressure of 0.4 bar, c) mixing the solution comprising the precipitate at a second temperature, wherein the second temperature has a value of 250° C. and is maintained for 80 min, such that ferrimagnetic iron oxide particles are obtained, and d) contacting the ferrimagnetic iron oxide particles with a solution of 5.3% w/v sodium silicate such that silanized ferrimagnetic iron oxide particles are obtained, wherein the step of contacting the ferrimagnetic iron oxide particles with the silicate solution comprises the steps of d1) sonificating the silicate solution comprising the ferrimagnetic iron oxide particles, d2) lowering the pH of the silicate solution to a value of 5 such that silanized ferrimagnetic iron oxide particles are obtained, d3) washing of the silanized ferrimagnetic particles with water, and d4) washing of the silanized ferrimagnetic particles with isopropanol such that crosslinking occurs within the silicate layer.

In some embodiments of the method described herein, step d) is repeated one or more times. Between the respective repetitions, the ferrimagnetic iron oxide particles are washed with a wash solution. Hence, in some embodiments, the method described herein comprises after step d) the additional step e): washing the silanized ferrimagnetic iron oxide particles one or more times with a wash solution. In some embodiments, the wash buffer in step e) is water, in some embodiments distilled or deionized water. In further embodiments, the wash buffer is isopropanol or an equivalent alcohol. The sequence of steps d) and e) is in some embodiments repeated one or more times. Where step d) comprises steps d1) to d4), the above-mentioned embodiments apply to the respective sequence of substeps from d1) to d4).

The repetition of step d) or the sequence of steps d) and e), respectively, result in particles with multiple layers of silica and silicates from sodium silicate precipitation. As shown in Example 4, such multiple-layered silanized ferrimagnetic iron oxide particles display enhanced nucleic acid binding properties.

In another aspect, the present invention relates to monodisperse silanized ferrimagnetic iron oxide particles for independent generic nucleic acid binding having the following characteristics: A core, wherein the core comprises an inner layer comprising $Fe_3O_4$ and an outer layer comprising $Fe_2O_3$, a coating, wherein the coating comprises silica and silicates from sodium silicate precipitation, a sedimentation speed in pure water of less than 60 µm/s, and no significant iron bleeding occurs on the particles in 1M HCl for at least 60 min.

In one embodiment, the difference in size of monodisperse silanized ferrimagnetic iron oxide particles is in average smaller than 5%. In a specific embodiment, the size of the particles is between 20 nm to 600 nm. In another embodiment, the size of the particles is 100 nm. In still another embodiment, the diameter of the particles is 100 nm. The size of the particles of one certain batch can be varied by adjusting the concentration of iron(II) salt in the liquid glycol. This however has to be understood that the size of the silanized ferrimagnetic iron oxide particles of one certain batch is essentially the same for all particles within that batch. Essentially the same size of the particles has to be interpreted in the context of this description such that the difference in size of the particles is in average smaller than 5%.

The monodisperse silanized ferrimagnetic iron oxide particles according to the description appear black in suspension. In one embodiment, the sedimentation speed of the monodisperse silanized ferrimagnetic iron oxide particles in pure water is less than 100 µm/s, less than 90 µm/s, less than 80 µm/s, less than 70 µm/s, less than 60 µm/s or less or equal than 50 µm/s. In a specific embodiment, the sedimentation speed of the monodisperse silanized ferrimagnetic iron oxide particles in pure water is 50 µm/s.

In one embodiment, the yield of the synthesis of the monodisperse silanized ferrimagnetic iron oxide particles is at least 20%, at least 30%, at least 40%, at least 50%, at least 60% or at least 70%. In a specific embodiment, the yield of the synthesis of the monodisperse silanized ferrimagnetic iron oxide particles is at least 75%.

As an alternative or an addition, for monodisperse silanized ferrimagnetic iron oxide particles that have multiple layers of coating as described in the context of the production method, the relative amount of coating on a specific particle or population of particles may be varied. For instance, the mass of coating may be, for instance, 20%, 40%, 60%, 80%, 100%, 120%. 140%, 160%, 180%, 200%, or other percentages relative to the mass of the respective iron oxide core. Such particles are used in Example 4.

In another aspect, the present invention relates to the use of the monodisperse silanized ferrimagnetic iron oxide particles as described in the previous paragraph for independent generic binding nucleic acid molecules. In one embodiment, the nucleic acid molecules are selected from the group consisting of RNA molecules and DNA molecules. In a specific embodiment, the nucleic acid molecules are DNA molecules. In a further embodiment, the nucleic acid molecules are RNA molecules.

As described supra, the binding of nucleic acids to magnetic particles is often part of a nucleic acid isolation or extraction procedure from essentially any source, such as cultured microorganisms, uncultured microorganisms, complex biological mixtures, tissues, sera, ancient or preserved tissues, environmental isolates or the like or from any "sample" that contains nucleic acid. Typically, one of the first steps of purification of a biological target material comprises releasing the contents of cells or viral particles by using enzymes and/or chemical reagents. This process is commonly referred to as "lysis". The nucleic acid to be isolated is ideally essentially unaffected by the lysis step. As known in the art, lysis procedures can involve chaotropic agents, ionic and/or non-ionic detergents such as SDS or sarcosyl, mechanic disruption by shearing forces or the like, French Press, ultrasound, liquid nitrogen, enzymes such as lysozyme or proteases, freeze-drying, heat or osmotic shock, cell membrane disruption under alkaline conditions, or other measures known by the person skilled in the art.

The released nucleic acid may then be bound to suitable binding particles such as the silanized ferrimagnetic iron oxide particles described herein. This binding step may involve the presence of chaotropic agents.

"Chaotropic agents" are substances that generally disturb the ordered structure of water molecules in solution and non-covalent binding forces in and between molecules. They can make several contributions to the isolation procedure. Chaotropic agents also contribute to the disruption of biological membranes, such as plasma membranes or the membranes of cell organelles, if present. Useful chaotropic agents in the context of the present invention include, but are not limited to, guanidinium salts such as guanidinium thiocyanate, guanidinium hydrochloride, guanidinium chloride or guanidinium isothiocyanate, urea, perchlorates such as potassium perchlorate, other thiocyanates or potassium iodide or sodium iodide. They can be applied as RNase inhibitors by disturbing the nuclease's tertiary structure. Usually, no further RNase inhibitor need to be applied to the lysis buffer when the biological target material is a nucleic acid. Also, chaotropic agents can play a significant role in the adhesive binding of nucleic acids to surfaces like glass. For lysis and/or binding purposes, chaotropic agents can be applied at a concentration of about 2 to about 8 M, and in some embodiments at a concentration of about 4 to about 6 M.

Further embodiments are included by the following items:
1. Method for producing a plurality of silanized ferrimagnetic iron oxide particles for independent generic nucleic acid binding, wherein the method comprises the steps of:
   a. Adding an iron(II) salt to a liquid glycol to obtain a solution,
   b. Raising the pH of the solution to a value of at least 9 such that a precipitate is obtained,
      wherein during steps a) and b) a first temperature is applied to the solution and wherein during steps a) and b) the solution is gassed with nitrogen,
   c. Mixing the solution comprising the precipitate at a second temperature such that ferrimagnetic iron oxide particles are obtained, and
   d. Contacting the ferrimagnetic iron oxide particles with a silicate solution such that silanized ferrimagnetic iron oxide particles are obtained.
2. The method of item 1, wherein contacting the ferrimagnetic iron oxide particles with a silicate solution comprises the steps of:
   d1. Sonificating the silicate solution comprising the ferrimagnetic iron oxide particles,
   d2. Lowering the pH of the silicate solution to a value of 6 or below such that silanized ferrimagnetic iron oxide particles are obtained,
   d3. Washing of the silanized ferrimagnetic particles with water, and
   d4. Washing of the silanized ferrimagnetic particles with isopropanol such that crosslinking occurs within the silicate layer.
3. Method of items 1-2, wherein the iron(II) salt is soluble in the liquid glycol.
4. Method of item 3, wherein the iron(II) salt soluble in the liquid glycol is selected from the group consisting of $FeCl_2$, $FeSO_4$, $FeAc_2$ and the hydrated forms thereof.
5. Method of items 1 to 4, wherein the liquid glycol is an alkyl glycol and polymerized forms thereof.
6. Method of item 5, wherein the alkyl glycol is selected from the group consisting of ethylene glycol, diethylene glycol, triethylene glycol, tetraethylene glycol, propylene glycol, dipropylene glycol, tripropylene glycol, tetraproylene glycol, butylene glycol, dibutylene glycol, tributylene glycol, tetrabutylene glycol.
7. Method of item 5, wherein the alkyl glycol is triethylene glycol.
8. Method of items 1-7, wherein the pH of the solution in step b) is raised to a value of 10.5.
9. Method of items 1-8, wherein the pH of the solution in step b) is raised using sodium hydroxide.
10. Method of items 1-9, wherein the first temperature has a value from 20 to 120° C.
11. Method of item 10, wherein the first temperature has a value of 100° C.
12. Method of item 11, wherein the first temperature is maintained for 5 to 60 min.
13. Method of items 1-12, wherein the second temperature has a value from 150 to 300° C.
14. Method of item 13, wherein the second temperature has a value of 250° C.
15. Method of item 14, wherein the second temperature is maintained for 20 min to 48 h.
16. Method of items 1-15, wherein the silicate is selected from the group consisting of potassium silicate and sodium silicate.
17. Method of items 1-16, wherein the silicate is present in the solution in a concentration from 1 to 30% w/v.
18. Method of item 17, wherein the silicate is present in the solution in a concentration of 5.3% w/v.
19. Method of items 2-18, wherein the pH of the solution in step d2) is lowered to a value of 5.
20. Method of item 19, wherein the pH of the solution in step d2) is lowered using an acid selected from the group consisting of phosphoric acid, sulphuric acid and hydrochloric acid.
21. Method of item 20, wherein the pH of the solution in step d2) is lowered using hydrochloric acid.
22. Method of items 1-21, wherein step d) is repeated one or more times.
23. Monodisperse silanized ferrimagnetic iron oxide particles for independent generic nucleic acid binding having the following characteristics:
a. A core, wherein the core comprises an inner layer comprising $Fe_3O_4$ and an outer layer comprising $Fe_2O_3$,
b. A coating, wherein the coating comprises silica and silicates from sodium silicate precipitation,
c. A sedimentation speed in pure water of less than 60 μm/s, and
d. No significant iron bleeding occurs on the particles in 1M HCl for at least 60 min.
24. The monodisperse silanized ferrimagnetic iron oxide particles according to item 23, wherein the difference in size of the monodisperse silanized ferrimagnetic iron oxide particles is in average smaller than 5%.
25. The monodisperse silanized ferrimagnetic iron oxide particles according to item 24, wherein the size of the particles n is between 20 nm and 600 nm.
26. Method for independent generic binding of nucleic acid molecules by use of the monodisperse silanized ferrimagnetic iron oxide particles of items 23-25.
27. Method of item 26, wherein the nucleic acid molecules are DNA molecules or RNA molecules.

EXAMPLES

The following examples 1 to 4 are provided to aid the understanding of the present invention, the true scope of which is set forth in the appended claims. It is understood that modifications can be made by a person of ordinary skill in the art to the procedures set forth below.

Example 1: Cleaning of the Reactor

The reactor used in the present description is a Büchi Midiclave Reactor with propeller stirrer and stream breaker from Hasteloy Steel.

Immediately after the removal of the ironoxide nanoparticle suspension, the flow break, agitator shaft and temperature sensor were washed 3 times with water.

The reactor was filled with 900 mL of a 0.02 M EDTA and 0.0067 M $FeCl_2$ solution and was heated to 120° C. and stirred with 1000 rpm for 15 h. The gasket ring between top panel and agitator vessel was removed and swiveled in 32% HCl for 30 seconds, than washed for 30 seconds under floating VE-$H_2O$.

Figure 2:
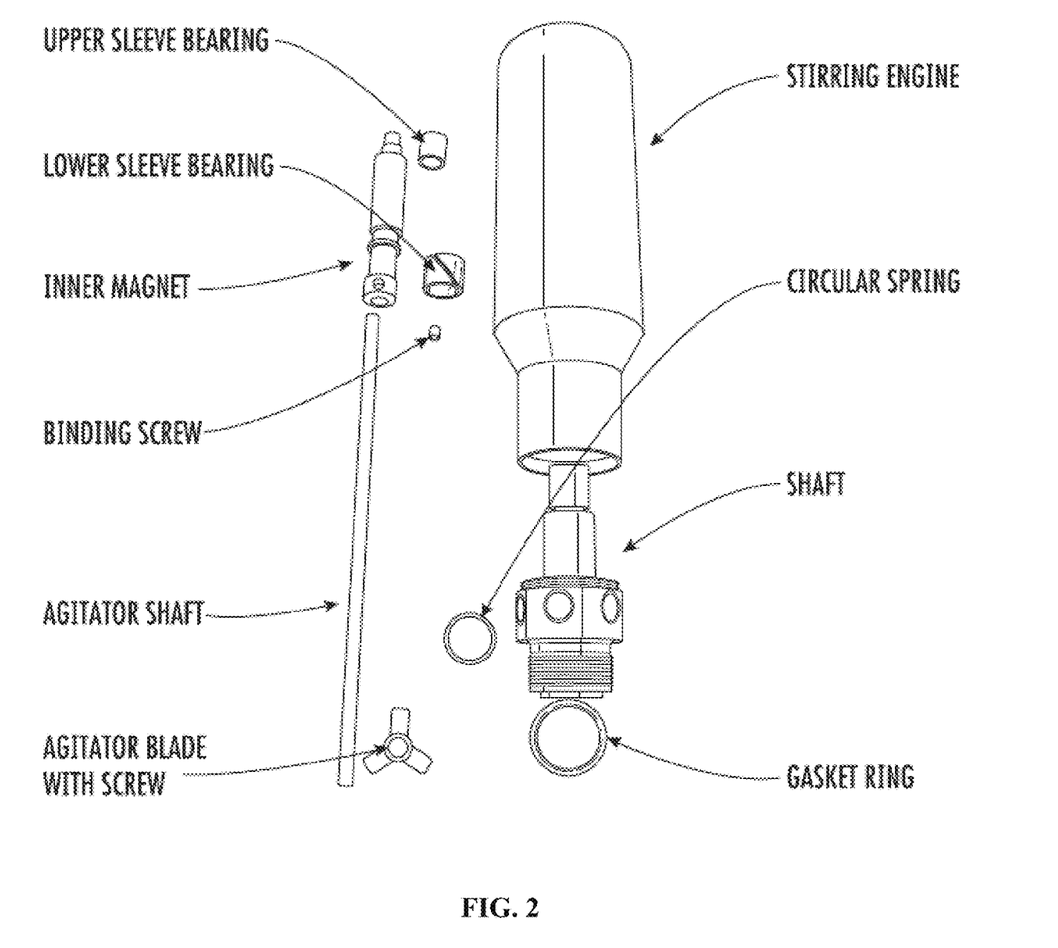
FIG. 2 Shows the labeled parts of the disassembled stirrer.

Temperature sensor, $N_2$-pipe, flow brake and agitator shaft are rinsed with VE-$H_2O$. The stirrer was removed and disassembled completely. The disassembled parts are shown and labeled in FIG. 2. The dissassembling was performed by the following steps: i) Remove wire on the top of the stirring engine, ii) pull the agitator shaft out, iii) unscrewe the stirring engine together with the shaft, iv) unscrewe the shaft out of the stirring engine (use the steel stick), v) remove gasket ring between top panel and shaft, vi) remove circular spring, vii) remove the upper sleeve bearing (use the fork), viii) release the binding screw between inner magnet and the agitator shaft and separate the parts, ix) strip down the lower sleeve bearing, and x) release the agitator blade screw and remove the agitator blade.

The shaft was washed for 30 seconds under floating VE-$H_2O$. In case of remaining impurities (brown/dark spots) in the shaft, the shaft was filled with HCl and subsequently floated with VE-$H_2O$. Then, the shaft was screwed back into the stirring engine. The swing gasket ring between top panel and shaft was rinsed for 30 seconds in 32% HCl and floated in VE-$H_2O$ for 30 seconds. The circular spring was washed for 30 seconds with VE-$H_2O$ and bigger particles were removed using forceps.

The inner magnet, binding screw, agitator shaft, stirring blade, stirring blade screw, upper and lower sleeve were rinsed in 30 seconds in 32% HCl and washed afterwards under floating VE-$H_2O$. The agitator shaft and the stirring blade are rebuilt with the stirring blade screw. The guide slot was lubrified with glycerin, put on the lower sleeve bearing and further lubricated on its outside. The inner magnet and the agitator shaft was assembled with the binding screw. The upper sleeve bearing was lubricated in its inside, put it on the inner magnet until it locks and then lubricated with glycerin on its outside. The flow break and the flow break pole was removed, rinsed them together with the screw nut in 32% HCl for 30 seconds, than wash it under floating VE-$H_2O$ for 30 seconds.

The outlet $N_2$-sleeve was removed. The sleeve clamp was loosened and the metal binding piece was pulled out. The binding piece was rinsed for 30 seconds in 32% HCl, then washed under floating VE-$H_2O$ for 30 seconds. Subsequently, the binding piece was inserted in the sleeve and fixed with the sleeve clamp.

Figure 3:
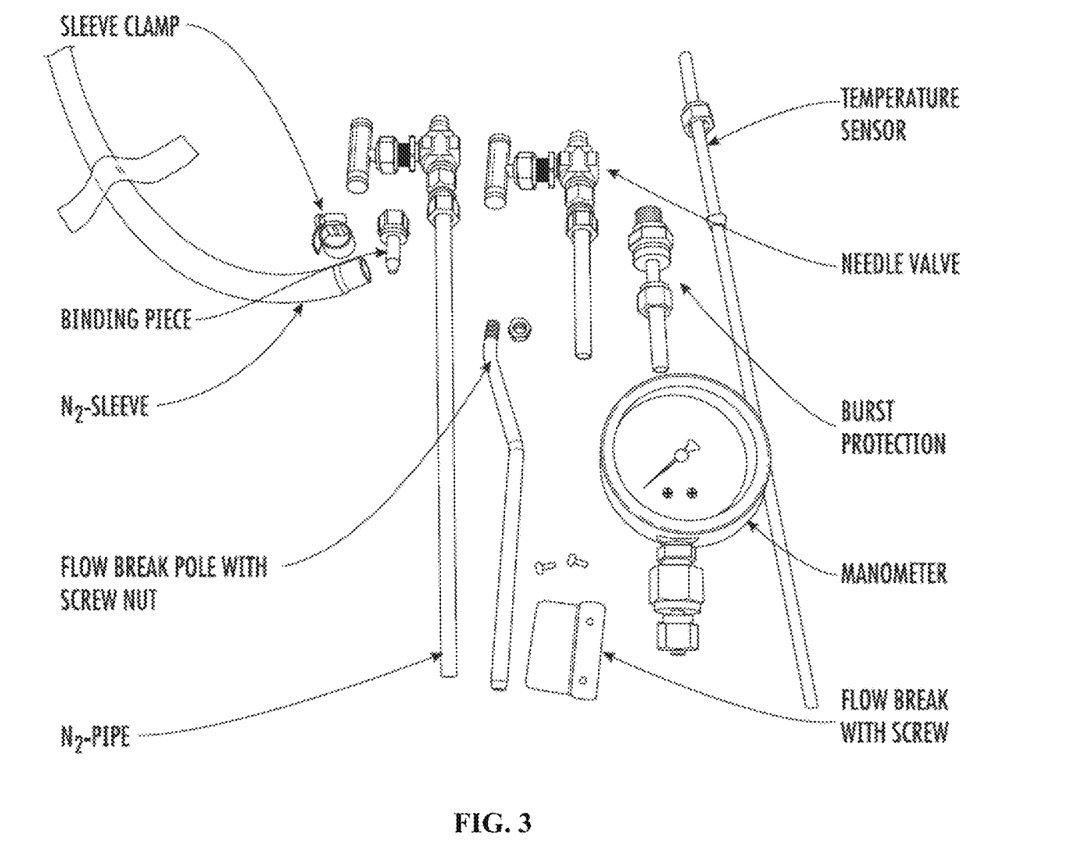
FIG. 3 Shows the manometer, temperature sensor, $N_2$-pipe, needle valve and burst protection and corresponding parts.

As a next step, manometer, temperature sensor, $N_2$-pipe, needle valve and burst protection was removed. The respective parts are shown and labeled in FIG. 3. Flush the manometer with VE-$H_2O$. The burst protection, needle valve and the $N_2$-pipe was cleaned with a cleaning cloth soaked in 32% HCl, followed by flushing it with a disposable pipette until the out coming HCl had no more visible colouring and washing it inside and outside under floating VE-$H_2O$ for 30 seconds.

The temperature sensor was cleaned with a cleaning cloth soaked in 32% HCl followed by washing it for 30 seconds with VE-$H_2O$.

Figure 4:
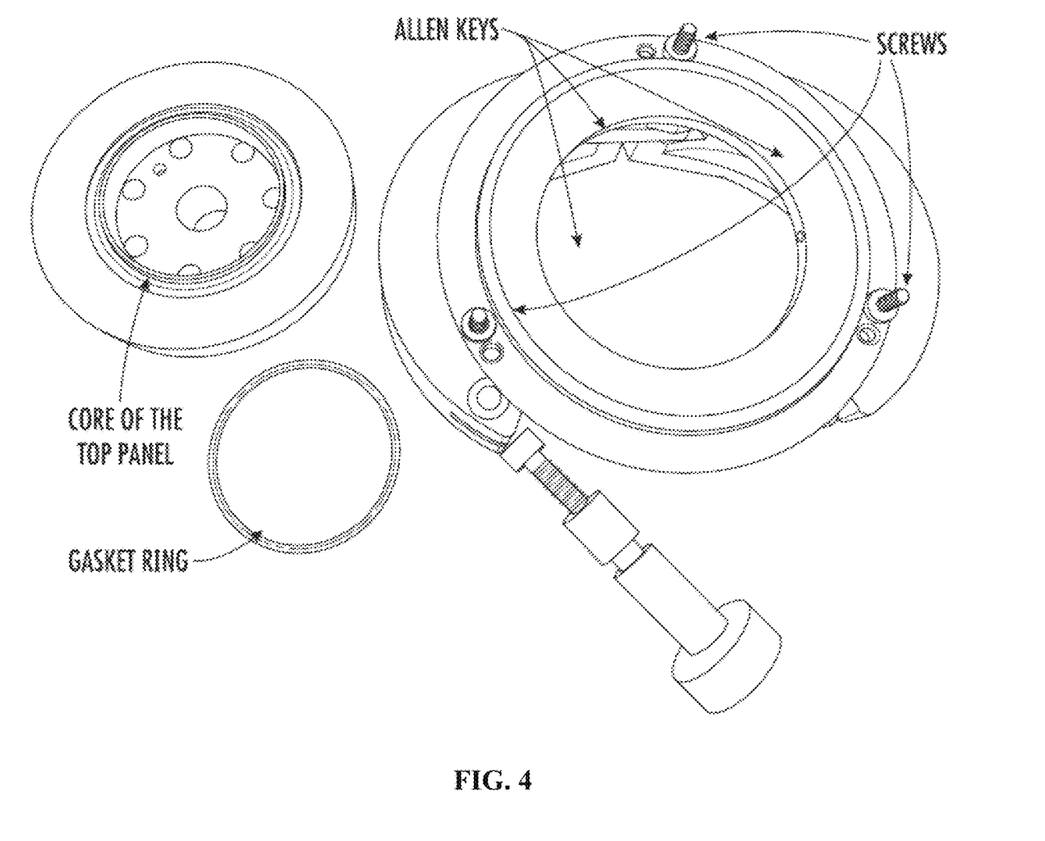
FIG. 4 Shows the core of the top panel and corresponding parts.

The three screws holding the top panel were solved and removed. Subsequently, the three allen keys which fix the core of the top panel were solved. See FIG. 4 showing the corresponding parts.

The core of the top panel (especially the seven screw holes) was cleaned with a disposable pipette with 32% HCl. The cleaning step was performed until the HCl did not show any visible yellow coloring. The core of the top panel was then washed under floating VE-H$_2$O for 30 seconds.

The two pressure sleeves at the agitator vessel were removed. The agitator vessel was washed for 90 seconds with 32% HCl. Subsequently, the agitator vessel was filled with 100 ml of 32% HCl and cleaned with a chemical resistant brush for 60 seconds. The HCl from the agitator vessel was discarded into a beaker. The last cleaning step was repeated twice. The agitator vessel was washed again for 90 seconds with 32% HCl. Finally, the agitator vessel was reassembled with the two pressure sleeves.

The core of the top panel was reassembled with the flow break. Then the manometer, temperature sensor, N$_2$-pipe, needle valve and burst protection was mounted back into the top panel. The gasket ring was placed between the shaft and the top panel. The stirring engine and the agitator shaft was inserted. The gasket ring was placed between top panel and agitator vessel.

The success of the cleaning procedure was controlled by filling the reassembled reactor with 1 L VE-H$_2$O. The reactor was heated to 150° C. for 60 minutes with 500 rpm. The step was repeated three times. After the third time of boiling, the VE-H$_2$O should have been clear, otherwise the cleaning procedure was repeated.

Example 2: Manufacturing of the Ferrimagnetic Iron Oxide Particles

Reaction equation: 3 FeCl$_2$+6 NaOH→Fe$_3$O$_4$+6 NaCl+H$_2$+2 H$_2$O 400 mL (4.21 mol) of triethylenglycol were put in a glas-reactor. While the reactor was heated to 100° C., stirring with the magnetic stirrer and introducing N$_2$ (pressure 0.4 bar at the outlet valve) into the triethylenglycol for 30 minutes was performed. Subsequently, 12.31 g FeCl$_2$*4 H$_2$O (60.8 mmol) and 12 mL NaOH (10 M) (120 mmol) were added to the triethylenglycol at 100° C. and still introducing N$_2$ while strengthen stirring (if necessary rise stirring speed) was continued for 10 minutes.

Transferring the glas-reactor content into a reactor which was preheated to 80° C. Stirring was performed for 10 minutes without further heating and introducing N$_2$. During continued stirring, the reactor was heated according to the protocol as depicted in FIG. 1. The temperature was increased from the preheated temperature of 80° C. to a value of 250° C. within a time period of 20 min. The value of 250° C. was maintained for a time period of 80 min. Subsequently, the second temperature was decreased to a value of 30° C. within a time period of 35 min.

After the reactor temperature reached 30° C. the pressure was released and the suspension was put into a beaker. The suspension was dialyzed over night in a 36/32 inch sleeve in Milli-Q-H$_2$O. The sleeve was soaked and washed for 10 minutes with Milli-Q-H$_2$O before filling it with particles. After dialyzing over night, the particles were filled into a Schott glas bottle. After sedimentation of the particles and removing the supernatant to a total volume of 50 mL, the suspension was transferred into a falkon tube.

Figure 5:
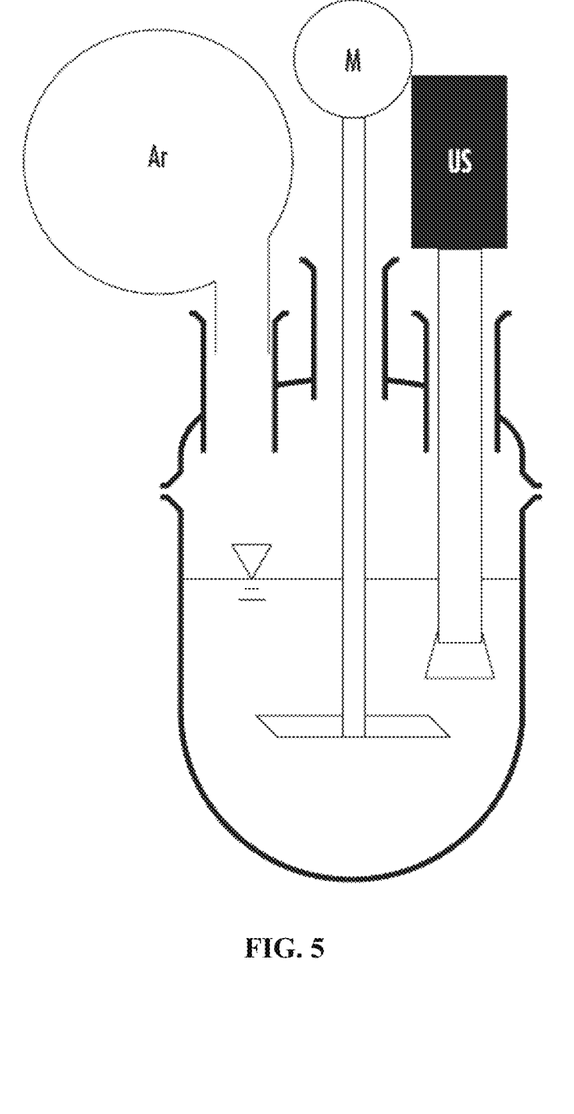
FIG. 5 Schematic drawing of the special design glas reactor used for silanizing the ferrimagnetic iron oxide particles. (Ar=Argon, M=Motor, US=Ultrasonic probe).

Example 3: Silanizing the Ferrimagnetic Iron Oxide Particles 300 mL of a 5.3% w/v silane solution were provided in a special design glas reactor 8 mL of the particle solution (0.5 g particle) as manufactured according to Example 2 were added. A schematic drawing of the special design glas reactor is presented in FIG. 5 (Ar=Argon, M=Motor, US=Ultrasonic probe). Sonification of the solution was performed using an ultrasonic probe every 50 seconds 5 times with 80% of the maximal amplitude energy intake for 200 ms. Subsequently, 100 mL of 1 M HCl was added followed by stirring at 300 rpm and continued use of the ultrasonic probe over night (with the same settings as mentioned above). Then, 10 mL of 1 M HCl was added and the solution was stirred for two more hours and an argon source drain was attached to the reactor to avoid oxygen in the atmosphere covering the solution. After sedimentation, the particles were washed with 400 mL VE-H$_2$O. After a further sedimentation of the particles, the supernatant was discarded. Subsequently, 300 mL silane solution was added to the particles. Sonification of the solution was performed every 50 seconds 5 times with 80% of the maximal amplitude energy intake for 200 ms. Subsequently, 100 mL of 1 M HCl was added followed by stirring at 300 rpm and continued use of the ultrasonic probe over night (same settings as mentioned above). Then, 10 mL of 1 M HCl was added and the solution was stirred for two more hours. After sedimentation, the particles were washed with 400 mL VE-H$_2$O. After a further sedimentation of the particles, the supernatant was discarded. The washing procedure was repeated 5 more times.

Example 4: Use of the Monodisperse Silanized Ferrimagnetic Iron Oxide Particles for Independent Generic Nucleic Acid Binding Monodisperse silanized ferromagnetic iron oxide particles produced according to the method described herein as exemplified in the Examples 1 to 3 were used for binding target nucleic acids from two different clinically relevant pathogenic organisms.

The particles exhibited different degrees of silanization, meaning that different relative amounts of coating were present on the particle surfaces. More specifically, the different percentages indicated in the tables below represent the mass of coating in relation to the mass of the respective iron oxide core. Hence, a suffix of "80%" denotes a population of particles wherein the coating mass is 80% of the iron oxide core mass.

Further, one set of particles was coated with two layers of silane, having been subjected to two consecutive rounds of silanization as described herein.

As a reference, magnetic glass particles from the commercially available MagNA Pure 96 DNA and Viral NA Large Volume Kit (Roche Diagnostics, Catalog No. 06374891001) were used in parallel experiments. Also, the reagents from the above-mentioned kit were used in a nucleic acid isolation procedure following the instructions of the user manual. The person skilled in the art is able to readily apply other procedures for using the particles described herein for binding nucleic acids. It is to be noted that for each experiment only 1 mg of the particles described herein were used, while the particles provided with the above-mentioned kit had to be used in portions of 12 mg for each experiment, according to the user manual.

After isolating the respective nucleic acids, they were subjected to realtime PCR on a LightCycler® 480 Analyzer (Roche Diagnostics) exploiting the commercially available kits listed in the following.

Isolation of Parvo B19 Virus (DNA)

Equipment:

| Name | Catalog. No. | Company |
|---|---|---|
| Parvo B 19 Quantification Kit | 0324680 809 | Roche Diagnostics |

PCR Results:

| Particles | Twice silanized run1 | Twice silanized run2 | Coating to core 00% [W/W] | Coating to core 80% [W/W] | Coating to core 20% [W/W] | 1 Kit particles run1 | Kit particles run2 |
|---|---|---|---|---|---|---|---|
| cp-mean | 25.37 | 25.64 | 26.05 | 27.86 | 25.56 | 26.54 | 25.28 |
| cp-min | 25.22 | 25.59 | 25.97 | 27.71 | 24.99 | 26.54 | 25.28 |
| cp-max | 25.52 | 25.69 | 26.10 | 28.02 | 25.84 | 26.54 | 25.28 |
| Δ cp max − cp min | 0.3 | 0.1 | 0.1 | 0.3 | 0.9 | 0.0 | 0.0 |
| Replicates | 2 | 2 | 4 | 3 | 5 | 1 | 1 |

Isolation of Influenza Virus (RNA)
Equipment:

| Name | Catalog No. | Company |
|---|---|---|
| Real Time ready RNA VirusMaster | 05 619 416 001 | Roche Diagnostics |
| Real Time ready Influenza A H1N1 Detection Set | 05 640 393 001 | Roche Diagnostics |

PCR Results:

| Particles | Twice silanized run1 | Twice silanized run2 | Coating to core 100% [W/W] | Coating to core 80% [W/W] | Coating to core 20% [W/W] | Kit particles run1 | Kit particles run2 |
|---|---|---|---|---|---|---|---|
| cp-mean | 29.12 | 29.14 | 32.48 | 34.73 | 31.31 | 29.90 | 29.97 |
| cp-min | 29.00 | 29.04 | 32.29 | 34.52 | 31.21 | 29.84 | 29.72 |
| cp-max | 29.23 | 29.24 | 32.65 | 34.90 | 31.44 | 29.96 | 30.22 |
| Δ cp max − cp min | 0.2 | 0.2 | 0.4 | 0.4 | 0.2 | 0.1 | 0.5 |
| Replicates | 2 | 2 | 4 | 4 | 4 | 2 | 2 |

The results clearly show that the particles produced by the method described herein are at least equivalent to the commercially available reference particles in their capacity to bind and thereby isolate target nucleic acids, comprising both DNA and RNA. Notably, the respective Cp (Crossing point) values which, in the current experimental setting, provide a measure for the nucleic acid yield following the binding/isolation procedure, are overall even improved. This is particularly evident for the twice-silanized particles produced by the method described herein, even though in all instances the mass of particles used was only a small fraction (1:12) of the mass of prior art particles.

In summary, it has been shown that the monodisperse silanized ferrimagnetic iron oxide particles of the present invention can be used for independent generic nucleic acid binding with properties that are as well or even better than particles used in the prior art, while displaying further advantageous properties with regard to their efficiency and their production procedure.

The invention claimed is:

1. A composition comprising monodisperse silanized ferrimagnetic iron oxide particles for independent generic nucleic acid binding wherein said particles comprise:
    (a) a core wherein the core consists of an inner layer consisting of $Fe_3O_4$ and an outer layer consisting of $Fe_2O_3$,
    (b) a coating wherein the coating comprises silica and silicates from sodium silicate precipitation,
        wherein said particles display a sedimentation speed in pure water of less than 60 μm/s, and no significant iron bleeding in 1M HCl for at least 60 minutes.
2. The composition of claim 1, wherein the difference in size of the monodisperse silanized ferrimagnetic iron oxide particles is in average smaller than 5%.
3. The composition of claim 1, wherein the size of the particles is between 20 nm and 600 nm.
4. The composition of claim 1, wherein the nucleic acid is a nucleic acid molecule that is a DNA molecule and/or RNA molecule.

* * * * *